(12) United States Patent
Yokota et al.

(10) Patent No.: US 7,484,529 B2
(45) Date of Patent: Feb. 3, 2009

(54) CONNECTOR

(75) Inventors: Takayuki Yokota, Nakakoma-gun (JP); Yoshinori Hishikawa, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 445 days.

(21) Appl. No.: 10/577,832

(22) PCT Filed: Nov. 2, 2004

(86) PCT No.: PCT/JP2004/016269
§ 371 (c)(1), (2), (4) Date: May 1, 2006

(87) PCT Pub. No.: WO2005/042069
PCT Pub. Date: May 12, 2005

(65) Prior Publication Data
US 2007/0073272 A1  Mar. 29, 2007

(30) Foreign Application Priority Data
Nov. 4, 2003  (JP)  ............................. 2003-374033

(51) Int. Cl.
*F16K 11/02* (2006.01)
*F16L 29/04* (2006.01)
(52) U.S. Cl. .................... 137/606; 251/149.6
(58) Field of Classification Search ............... 137/602, 137/605, 606, 861, 877, 878, 881; 251/149, 251/149.1, 149.4, 149.6; 604/167.04, 244, 604/246
See application file for complete search history.

(56) References Cited

U.S. PATENT DOCUMENTS 4,449,693 A  5/1984  Gereg (Continued)

FOREIGN PATENT DOCUMENTS

JP  5-32071 B2  5/1993

(Continued)

OTHER PUBLICATIONS

International Search Report dated Feb. 1, 2005.

(Continued)

*Primary Examiner*—Stephen M Hepperle
*Assistant Examiner*—William McCalister
(74) *Attorney, Agent, or Firm*—Buchanan Ingersoll & Rooney PC (57) ABSTRACT

A connector having a male-side connection section, a liquid flow section where a liquid flow space communicating with the inside of the male-side connection section is provided, a first female-side connection opening and a second female-side connection opening, and a first valve body and a second valve body that are made from an elastic material. A side slit of the first valve body and a side slit of the second valve body face the liquid flow space. When a tube body is connected to the first female-side connection opening, the inside of the tube body and the inside of the male-side connection section are communicated through a top slit, the side slit, and the liquid flow space. When a tube body is connected to the second female-side connection opening, the inside of the tube body and the inside of the male-side connection section are communicated through a top slit, the side slit, and the liquid flow space.

18 Claims, 9 Drawing Sheets

U.S. PATENT DOCUMENTS

| | | | | |
|---|---|---|---|---|
| 5,201,725 | A | * | 4/1993 | Kling .................. 604/284 |
| 5,273,533 | A | | 12/1993 | Bonaldo |
| 5,501,426 | A | | 3/1996 | Atkinson et al. |
| 5,509,912 | A | * | 4/1996 | Vaillancourt et al. ........ 604/537 |
| 5,676,346 | A | | 10/1997 | Leinsing |
| 2002/0017127 | A1 | * | 2/2002 | Nakano et al. ............. 73/31.05 |
| 2003/0036735 | A1 | * | 2/2003 | Jepson et al. ............... 604/247 |
| 2007/0028979 | A1 | * | 2/2007 | Yokota et al. ............... 137/877 |
| 2007/0218745 | A1 | * | 9/2007 | Yokota et al. ............... 439/357 |

FOREIGN PATENT DOCUMENTS

| | | |
|---|---|---|
| JP | 9-108361 A | 4/1997 |
| JP | 3052138 U | 9/1998 |
| JP | 2002-035140 A | 2/2002 |
| JP | 2003-144546 A | 5/2003 |
| WO | 89/06553 A2 | 7/1989 |

OTHER PUBLICATIONS

International Report by the Searching Authority dated Feb. 1, 2005.
U.S. Appl. No. 10/577,662, filed May 1, 2006, Takayuki Yokota et al.

* cited by examiner

CONNECTOR

TECHNICAL FIELD

The present invention relates to a connector having a valve mechanism for opening and closing a flow passage when a tube is connected and disconnected.

BACKGROUND ART

Medical circuits for use in fluid infusion, blood infusion, parenteral nutrition administration, etc. are occasionally connected and disconnected for continuously or temporarily supplying fluids such as a plurality of medicinal solutions, blood, liquid diet, etc. It is well known in the art that connectors are incorporated those medical circuits for connection and disconnection (see, for example, Japanese Laid-Open Patent Publication No. 9-108361 and Japanese Patent Publication No. 5-32071).

A typical one of the connectors is a three-way cock. The three-way cock comprises a single male lure connector and two female lure connectors which are fitted to each other to connect the circuit. However, the three-way cock is disadvantageous in that it is vulnerable to bacterial contamination because a fluid passage region thereof is exposed to external air when the circuit is disconnected. Particularly, the female joint is frequently brought into contact with external air because it is used many times for repeated connection and disconnection.

There is known a connector having a valve body in a female joint port for preventing a fluid passage region thereof from being exposed to external air. According to the connector, the valve body is pierced by a needle or a male connector is inserted into the valve body that has a slit, opening the fluid passage. After the needle or the male connector is removed, the valve body is closed again, preventing the fluid passage from being exposed to external air.

However, the above connectors are problematic in that since the valve body is mounted in only one female joint port, when the male connector is removed from the other female joint port, the female joint port is exposed to the atmospheric air.

The above connectors are also disadvantageous in that the female joint ports tend to trap a fluid, making it difficult for a medical solution to flow in its entirety, so that an environment for easy bacterial growth tends to be created. Furthermore, though the connector needs to be filled with a fluid such as a medical solution or the like before it is used, existing air in the connector cannot easily be removed.

Further, when a needle or a male connector is attached to and removed from a female joint port, the contents of the connector are liable to change. For example, if the contents of the connector increase when the male connector is removed, the blood flows from a blood vessel catheter connected to the connector back into the blood vessel catheter, causing the blood vessel catheter to be closed off.

DISCLOSURE OF THE INVENTION

It is an object of the present invention to provide a connector which is capable of preventing a flow passage from being contaminated by reliably opening and closing the flow passage, as a tube is connected and disconnected, and which makes a fluid less liable to be trapped therein.

To achieve the above object, a connector according to the present invention comprises:
a tubular male joint member;
a liquid passage portion having a liquid passage space defined therein in fluid communication with an interior of the male joint member;
a first female joint port and a second female joint port each of which is capable of receiving a tube;
a first valve body made of an elastic material and having a top slit defined in a top thereof and a side slit defined in a side thereof, the first valve body being deformable to open the top slit and the side slit when the tube is connected to the first female joint port; and
a second valve body made of an elastic material and having a top slit defined in a top thereof and a side slit defined in a side thereof, the second valve body being deformable to open the top slit and the side slit when the tube is connected to the second female joint port;
wherein the side slit of the first valve body and the side slit of the second valve body face the liquid passage space;
when the tube is connected to the first female joint port, an interior of the tube and the interior of the male joint member communicate with each other through the top slit and the side slit of the first valve body and the liquid passage space; and
when the tube is connected to the second female joint port, an interior of the tube and the interior of the male joint member communicate with each other through the top slit and the side slit of the second valve body and the liquid passage space.

With the above arrangement, since the flow passage is reliably opened and closed when the tube is connected and disconnected, the flow passage is prevented from being contaminated. The connector is also prevented from developing regions therein where the liquid is trapped.

In the connector according to the present invention, the first female joint port or the second female joint port and the male joint member preferably have respective central lines extending substantially parallel to each other.

In the connector according to the present invention, the liquid passage portion, the first valve body, and the second valve body are preferably integrally formed with each other.

In the connector according to the present invention, at least one of the first female joint port and the second female joint port is preferably axially movable relatively to the corresponding valve body.

In the connector according to the present invention, the first valve body and the second valve body preferably have respective central lines staggered with respect to each other.

In the connector according to the present invention, the first female joint port is preferably axially movable relatively to the first valve body, and the second female joint port is preferably axially movable relatively to the second valve body.

To achieve the above object, a connector according to the present invention comprises:
a tubular male joint member;
a liquid passage portion having a liquid passage space defined therein in fluid communication with an interior of the male joint member;
a housing having a female joint port which is capable of receiving a tube; and
a valve body made of an elastic material and housed in the housing, the valve body being fixedly disposed with respect to the male joint member and having a top slit defined in a top thereof and a side slit defined in a side thereof, the valve body being deformable to open the top slit and the side slit when the tube is connected to the female joint port;
wherein the side slit of the valve body faces the liquid passage space;
the housing is axially movable relatively to the valve body;
when the tube is to be connected to the female joint port, the housing is moved with respect to the valve body to insert the tube into the female joint port; and when the tube is connected to the female joint port, an interior of the tube and the interior of the male joint member communicate with each other through the top slit and the side slit of the valve body and the liquid passage space.

With the above arrangement, since the flow passage is reliably opened and closed when the tube is connected and disconnected, the flow passage is prevented from being contaminated. The connector is also prevented from developing regions therein where the liquid is trapped.

The connector according to the present invention preferably has a solid pin for being inserted into the top slit to spread the top slit when the tube is connected.

To achieve the above object, a connector according to the present invention comprises:

a tubular male joint member;

a liquid passage portion having a liquid passage space defined therein in fluid communication with an interior of the male joint member;

a female joint port which is capable of receiving a tube;

a valve body made of an elastic material and having a top slit defined in a top thereof, a side slit defined in a side thereof, and a hollow space, the valve body being deformable to open the top slit and the side slit when the tube is connected to the female joint port; and a solid pin positioned in the hollow space of the valve body;

wherein the side slit of the valve body faces the liquid passage space;

when the tube is connected to the female joint port, the tube presses a top surface of the valve body to compress the valve body axially, thereby opening the side slit and inserting the pin into the top slit to spread the top slit, so that an interior of the tube and the interior of the male joint member communicate with each other through the top slit and the side slit of the valve body and the liquid passage space.

With the above arrangement, since the flow passage is reliably opened and closed when the tube is connected and disconnected, the flow passage is prevented from being contaminated. The connector is also prevented from developing regions therein where the liquid is trapped.

In the connector according to the present invention, the liquid passage space is preferably of a shape for preventing a liquid from being trapped therein when the liquid flows in the liquid passage space.

In the connector according to the present invention, the solid pin preferably fills up the hollow space of the valve body substantially without clearances, when the tube is not connected to the female joint port.

BEST MODE FOR CARRYING OUT THE INVENTION

A connector according to the present invention will be described in detail below based on a preferred embodiment shown in the accompanying drawings.

Figure 1:
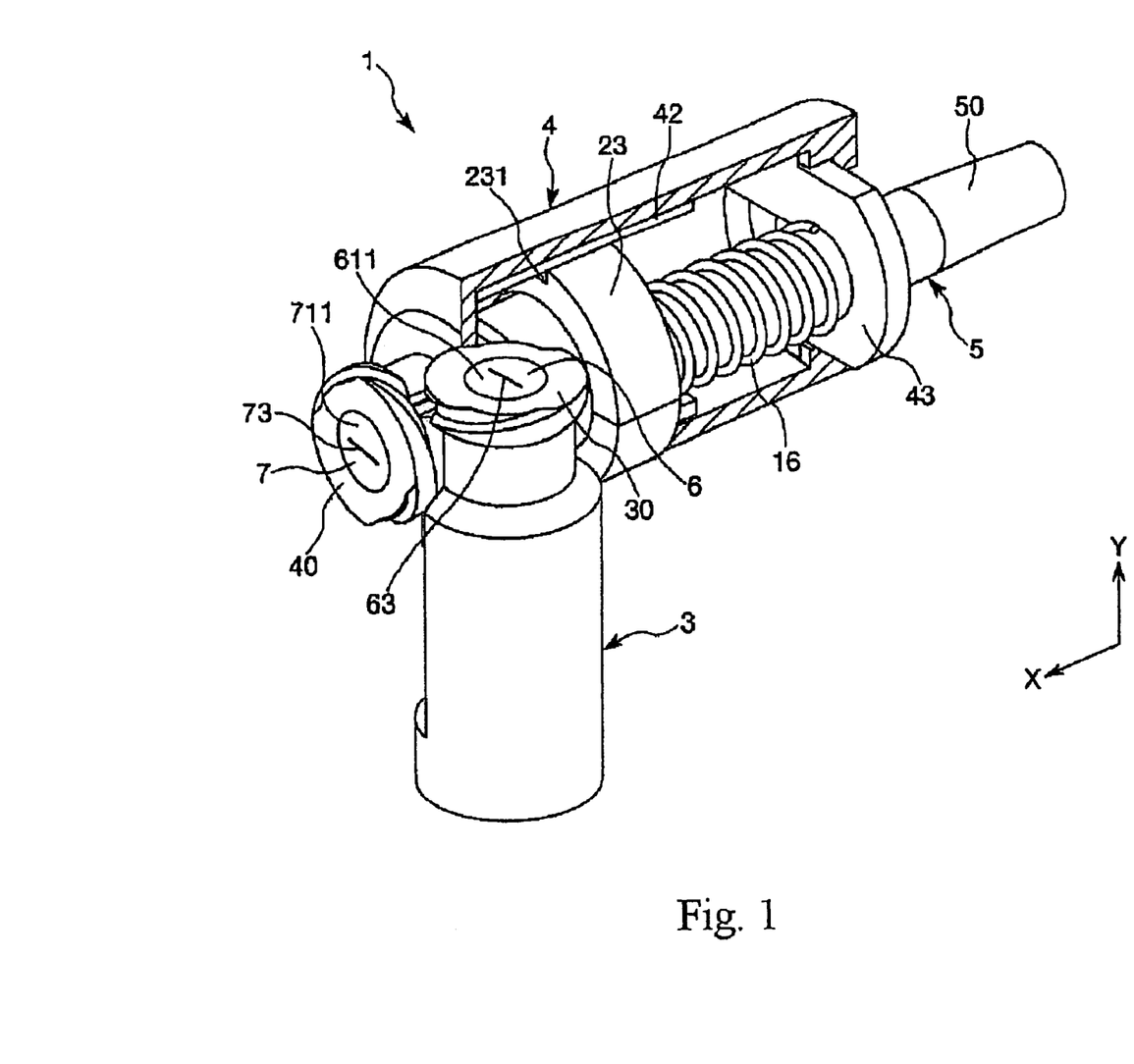
FIG. 1 is a perspective view, partly in cross section, of a connector according to an embodiment of the present invention.
Figure 2:
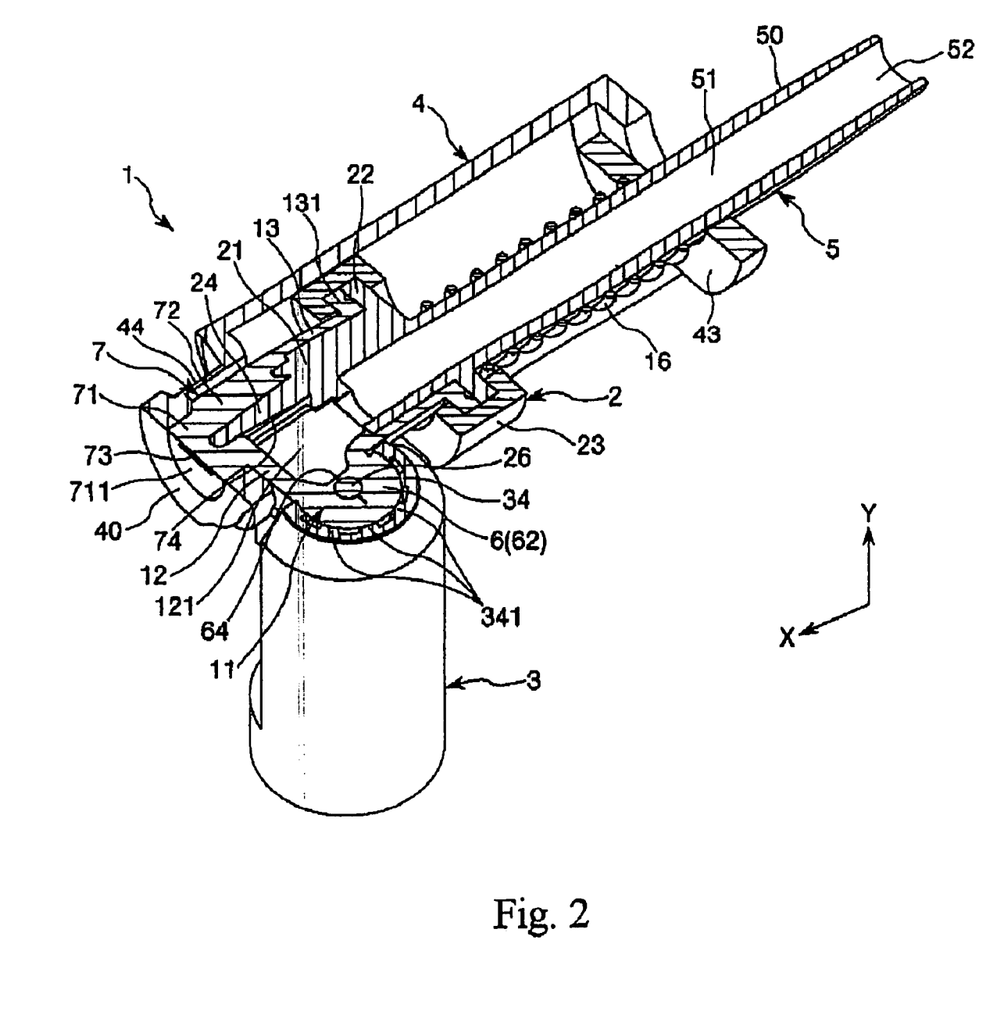
FIG. 2 is a sectional perspective view of the connector shown in FIG. 1.
Figure 3:
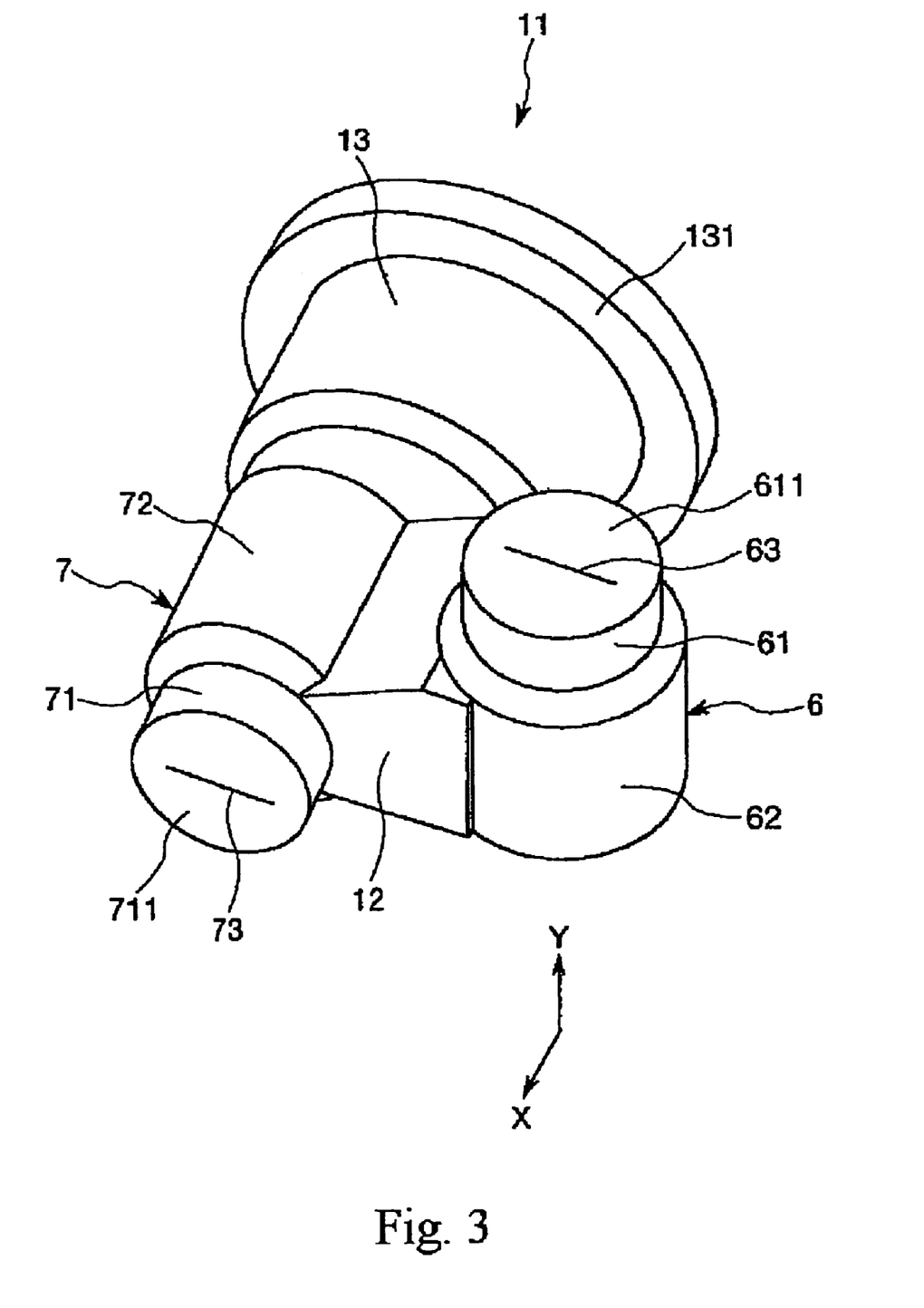
FIG. 3 is a perspective view of a valve assembly incorporated in the connector shown in FIG. 1.
Figure 4:
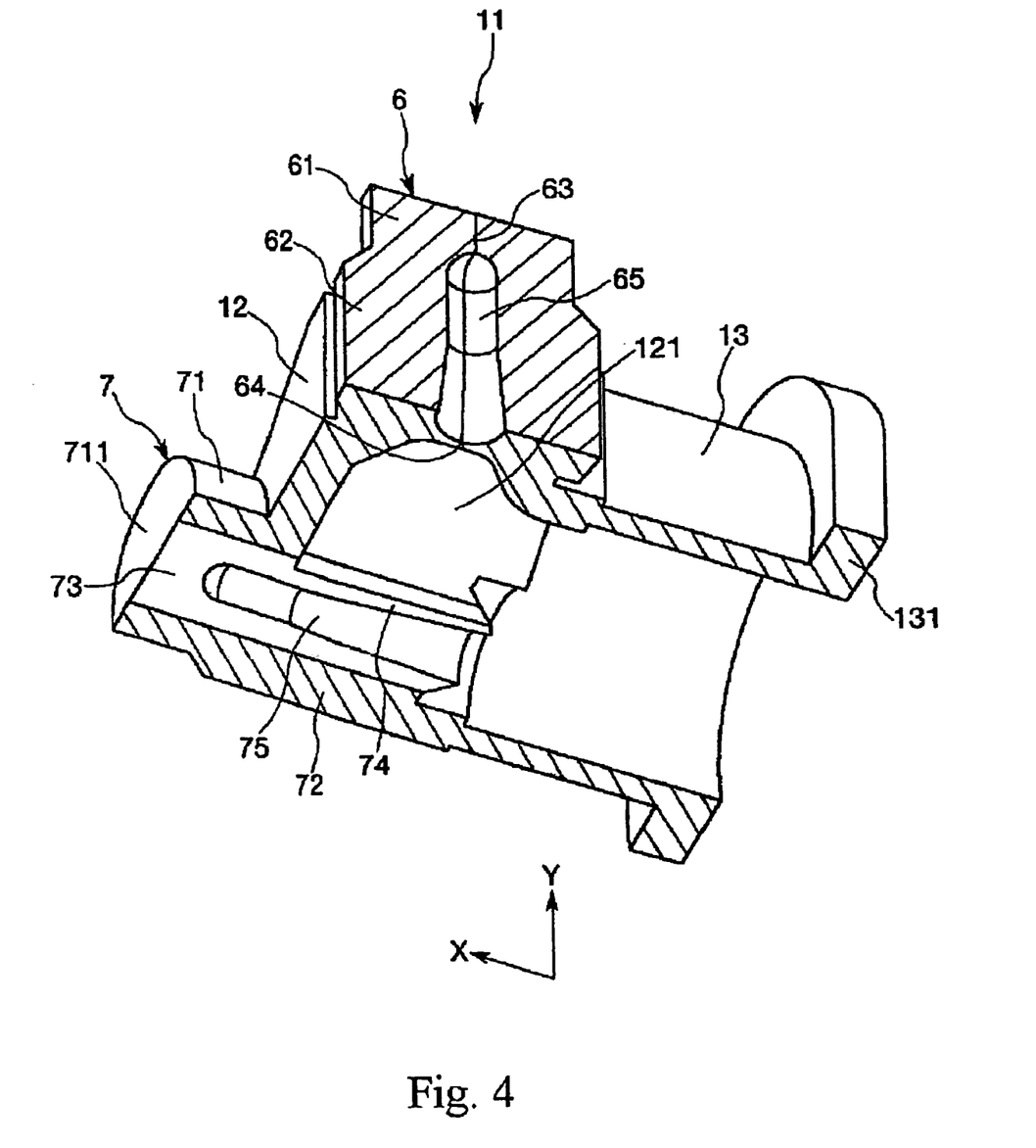
FIG. 4 is a sectional perspective view of the valve assembly incorporated in the connector shown in FIG. 1.

FIG. 1 is a perspective view, partly in cross section, of a connector according to an embodiment of the present invention, FIG. 2 is a sectional perspective view of the connector shown in FIG. 1, FIGS. 3 and 4 are a perspective view and a sectional perspective view, respectively of a valve assembly incorporated in the connector shown in FIG. 1, and FIGS. 5 through 9 are sectional perspective views, respectively, of the connector shown in FIG. 1.

A connector 1 shown in these figures is used in combination with a medical instrument which needs to be connected to a fluid flow passage, such as a fluid infusion set (blood infusion set), a parenteral nutrition set, a pressure monitoring line, an artificial lung circuit, an artificial dialysis circuit, etc.

As shown in FIG. 1, the connector 1 has a first female joint port 30 and a second female joint port 40 which are capable of receiving a tube therein, a male joint member 50, a first valve body 6 disposed in the first female joint port 30, and a second valve body 7 disposed in the second female joint port 40.

Tubes which provide flow passages (e.g., a projecting tip end of a syringe, an independent hub or sheath, or the like) can be inserted into and connected to the first female joint port 30 and the second female joint port 40, respectively.

The first female joint port 30 and the second female joint port 40 have respective central lines, which are skew lines and angularly spaced from each other by about 90°. In the description which follows, a direction parallel to the central line of the first female joint port 30 will be referred to as "Y-axis direction", and a direction parallel to the central line of the second female joint port 40, i.e., a direction perpendicular to the Y-axis direction, as "X-axis direction".

The male joint member 50 comprises a tubular member with a flow passage 51 defined therein and has its central line extending in the X-axis direction. The male joint member 50 has a lure taper whose outside diameter is progressively reduced toward its tip end. The male joint member 50 can be inserted into and connected to a female joint port of another instrument (e.g., an opening in the proximal end of a catheter hub).

A plurality of connectors 1 may be put together and may have their male joint members 50 inserted into and connected to the second female joint ports 40 of the other connectors 1, so that the connectors 1 can be used as an interconnected assembly. Since the second female joint ports 40 and the male joint members 50 are oriented parallel to each other and open away from each other, the connectors 1 can be connected in a linear array and hence can be connected in a form that can easily be used.

The first female joint port 30 is defined as part of a housing 3. The housing 3 is substantially in the form of a hollow cylinder with a side surface thereof being cut off, and has the first female joint port 30 on an end thereof.

The second female joint port 40 is defined as part of a housing 4. The housing 4 is substantially in the form of a hollow cylinder with a side surface thereof being cut off, and has the second female joint port 40 on an end thereof.

As shown in FIG. 2, a tubular member 5 is inserted in the housing 4. The tubular member 5 has an end portion (remote from the second female joint port 40) serving as the male joint member 50.

A support body 2 is disposed on the other end of the tubular member 5, and supports a valve assembly 11. The tubular member 5 has a flow passage 51 defined therein which has an end communicating with a liquid passage space 121 defined in the valve assembly 11.

As shown in FIG. 3, the valve assembly 11 comprises a first valve body 6, a second valve body 7, a liquid passage portion 12, and a fixed member 13 which are integrally formed of an elastic material.

The valve assembly 11 (the first valve body 6 and the second valve body 7) is not limited to any particular material, but should preferably be a material having appropriate elasticity and restorability, e.g., any of various rubber materials such as silicone rubber or the like or any of various thermoplastic resins such as polybutadiene, EVA, styrene-based elastomer, or the like.

The first valve body 6 comprises a substantially cylindrical barrel 62 having a central line extending parallel to the Y-axis direction and a top (head) 61 slightly smaller in diameter than the barrel 62. The top 61 has a top slit 63 defined therein which reaches (extends through the top 61 to) a top surface 611.

The second valve body 7 comprises a substantially cylindrical barrel 72 having a central line extending parallel to the X-axis direction and a top (head) 71 slightly smaller in diameter than the barrel 72. The top 71 has a top slit 73 defined therein which reaches (extends through the top 71 to) a top surface 711.

The first valve body 6 and the second valve body 7 have respective central lines, which are skew lines, and have respective sides joined to each other through the liquid passage portion 12. The fixed member 13 is substantially in the form of a hollow cylinder which is greater in outside diameter than the first valve body 6, and has a flange 131 on an end thereof.

As shown in FIG. 4, the liquid passage portion 12 has the liquid passage space (bore) 121 defined therein. The liquid passage space 121 is of a shape for preventing a liquid from being trapped as much as possible when the liquid flows therein. Stated otherwise, the liquid passage space 121 is of a shape which does not have any portions such as a bay where the liquid tends to be trapped.

Since the central lines of the first valve body 6 and the second valve body 7 are skew lines, the connector 1 is advantageous in that the volume of the liquid passage space 121 is much smaller than if those central lines intersect on the same plane.

The barrel 62 of the first valve body 6 has a side slit 64 defined in a side (side wall) thereof. The side slit 64 has an outer side facing the liquid passage space 121. In the illustrated arrangement, the top slit 63 and the side slit 64 are continuously defined on the same plane. However, the top slit 63 and the side slit 64 may be defined so as to partly cross each other three-dimensionally.

The barrel 62 has a substantially cylindrical pin insertion space (hollow) 65 defined concentrically therein. The pin insertion space 65 and the liquid passage space 121 are separated from each other by the side wall in which the side slit 64 is defined.

The barrel 72 of the second valve body 7 has a side slit 74 defined in a side (side wall) thereof. The side slit 74 has an outer side facing the liquid passage space 121. In the illustrated arrangement, the top slit 73 and the side slit 74 are continuously defined on the same plane. However, the top slit 73 and the side slit 74 may be defined so as to partly cross each other three-dimensionally.

The barrel 72 has a substantially cylindrical pin insertion space (hollow) 75 defined concentrically therein. The pin insertion space 75 and the liquid passage space 121 are separated from each other by the side wall in which the side slit 74 is defined.

As shown in FIG. 2, the valve assembly 11 is supported on and fixed to the support body 2. The support body 2 has an insert 21 inserted in the fixed member 13 and a flange 22 superposed on the flange 131 of the fixed member 13. The insert 21 and the flange 22 are integrally formed with the tubular member 5. The support body 2 has a fixing member 23 gripping the flange 131 and the flange 22, which are superposed on each other, fully circumferentially, thereby fixing the valve assembly 11 to the support body 2 in a light-tight fashion. The fixing member 23 is formed separately from the tubular member 5.

The insert 21 has a flow passage defined therein which is contiguous to the flow passage 51 in the male joint member 50 and is in fluid communication with the liquid passage space 121 in the valve assembly 11.

The support body 2 also has a solid pin 24 positioned in the pin insertion space 75 in the second valve body 7. The pin 24 is integrally formed with the insert 21. The pin 24 is of a shape filling up the pin insertion space 75 substantially without clearances when a male lure (tube) 200 is not connected to the second female joint port 40 (this state will hereinafter be referred to as "unconnected state"). The pin 24 that fills up the pin insertion space 75 is effective to prevent a liquid from being trapped in the pin insertion space 75. Since the pin 24 is a solid member free of hollow spaces therein, it also prevents a liquid from being trapped therein.

Figure 5:
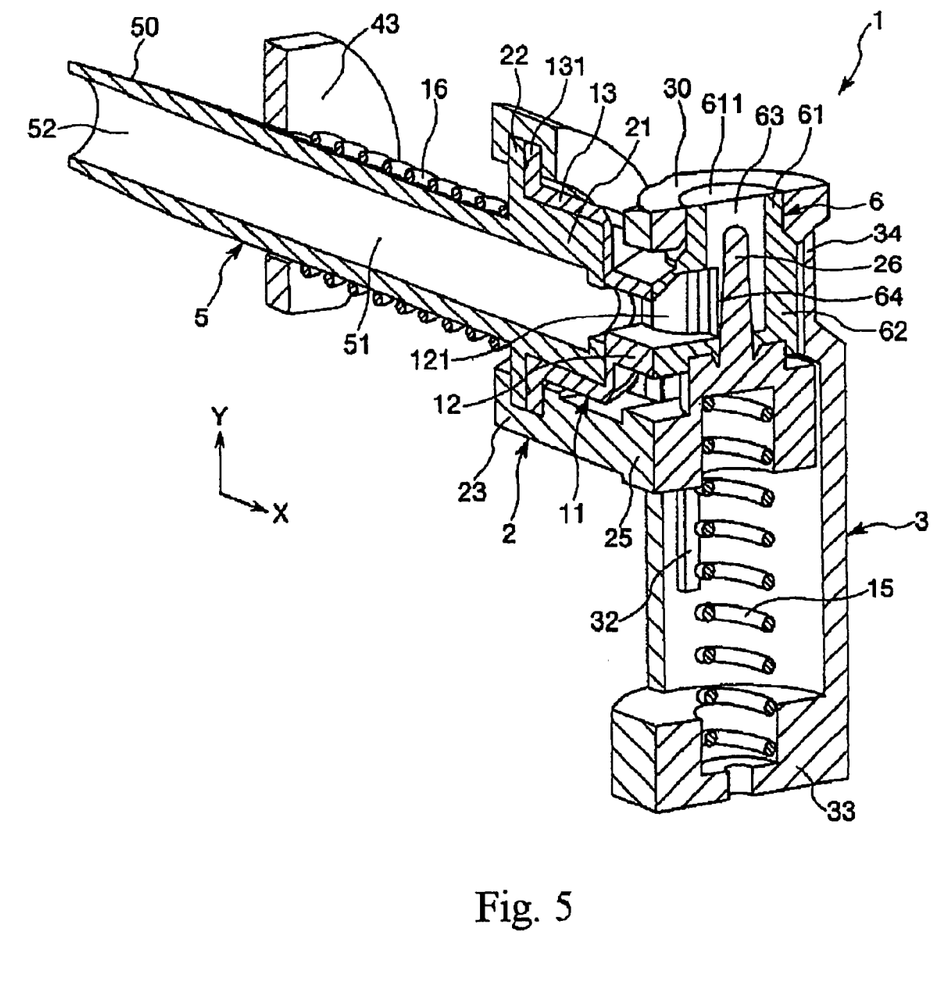
FIG. 5 is a sectional perspective view of the connector shown in FIG. 1.

As shown in FIG. 5, the support body 2 further has a base 25 supporting the first valve body 6 thereon and a solid pin 26 positioned in the pin insertion space 65 in the first valve body 6. The base 25 and the pin 26 are integrally formed with the fixing member 23. The pin 26 is of a shape filling up the pin insertion space 65 substantially without clearances when a male lure (tube) 100 is not connected to the first female joint port 30 (this state will hereinafter be referred to as "unconnected state"). The pin 26 that fills up the pin insertion space 65 is effective to prevent a liquid from being trapped in the pin insertion space 65. Since the pin 26 is a solid member free of hollow spaces therein, it also prevents a liquid from being trapped therein.

The housing 3 is slidable against the support body 2 and is movable in a direction (the Y-axis direction) perpendicular to the top surface 611 of the first valve body 6. In the illustrated arrangement, the direction of movement of the housing 3 is limited to the Y-axis direction by a ridge 32 disposed on an inner surface of the side wall of the housing 3 and extending in the Y-axis direction and a groove (not shown) defined in the base 25 of the support body 2, the ridge 32 and the groove being fitted to each other for guiding the housing 3.

A helical spring 15 is disposed between a bottom surface 33 of the housing 3 and the base 25 for normally urging the housing 3 to return to the position in the unconnected state shown in FIG. 5 when the housing 3 is moved in the Y-axis direction.

In the unconnected state, the top 61 of the first valve body 6 is inserted in the first female joint port 30. The inside diameter of the first female joint port 30 is slightly smaller than the outside diameter of the top 61 in its free state. In the unconnected state, therefore, the top 61 is tightened radially, reliably closing the top slit 63.

In the unconnected state, the barrel 62 of the first valve body 6 is positioned in a neck 34 of the housing 3. The inside diameter of the neck 34 is substantially the same as the outside diameter of the barrel 62. In the unconnected state, the neck 34 holds the barrel 62, holding the pin insertion space 65 and the pin 26 in reliable alignment with each other and reliably closing the side slit 64.

As shown in FIG. 2, the neck 34 has a plurality of ribs (ridges) 341 extending axially on an inner circumferential surface thereof. The area of contact between the neck 34 and the barrel 62 is thus reduced to suppress sliding resistance therebetween.

As shown in FIG. 1, the housing 4 is slidable against the support body 2 and is movable in a direction (the X-axis direction) perpendicular to the top surface 711 of the second valve body 7. In the illustrated arrangement, the direction of movement of the housing 4 is limited to the X-axis direction by a ridge 42 disposed on an inner surface of the side wall of the housing 4 and extending in the X-axis direction and a groove 231 defined in the fixing member 23 of the support body 2, the ridge 42 and the groove 231 being fitted to each other for guiding the housing 4.

As shown in FIG. 2, a helical spring 16 is disposed between a bottom surface 43 of the housing 4 and the support body 2 for normally urging the housing 4 to return to the position in the unconnected state shown in FIGS. 1 and 2 when the housing 4 is moved in the X-axis direction. The tubular member 5 is inserted in the helical spring 16.

In the unconnected state, the top 71 of the second valve body 7 is inserted in the second female joint port 40. The inside diameter of the second female joint port 40 is slightly smaller than the outside diameter of the top 71 in its free state. In the unconnected state, therefore, the top 71 is tightened radially, reliably closing the top slit 73.

In the unconnected state, the barrel 72 of the second valve body 7 is positioned in a neck 44 of the housing 4. The inside diameter of the neck 44 is substantially the same as the outside diameter of the barrel 72. In the unconnected state, the neck 44 holds the barrel 72, holding the pin insertion space 75 and the pin 24 in reliable alignment with each other and reliably closing the side slit 74. The neck 44 has ribs similar to the ribs 341 on an inner circumferential surface thereof.

A state of the connector 1 when the male lure 100 such as those used in a fluid infusion set is connected to the first female joint port 30 will be described below with reference to FIGS. 6, 7, and 8. FIG. 7 is a view similar to FIG. 6 with the male lure 100 omitted from illustration.

Figure 6:
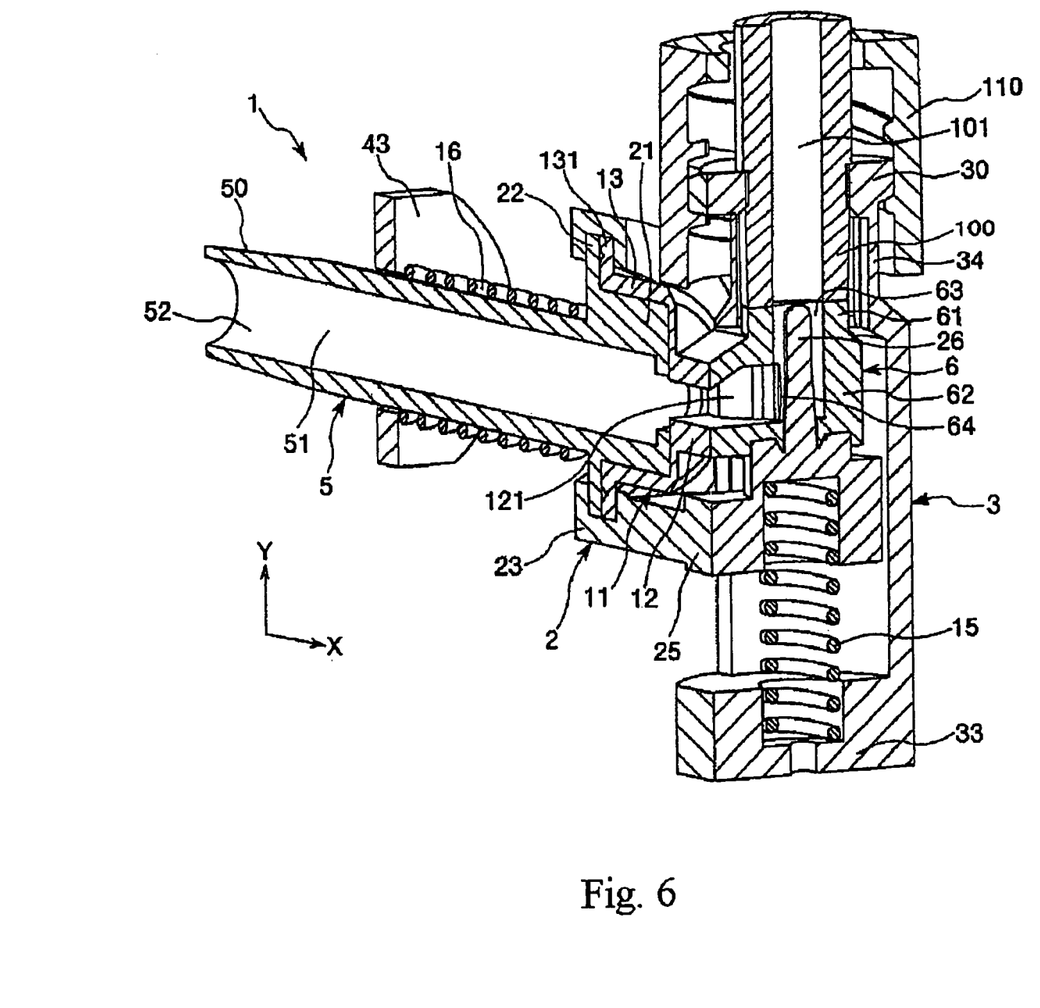
FIG. 6 is a sectional perspective view of the connector shown in FIG. 1.
Figure 7:
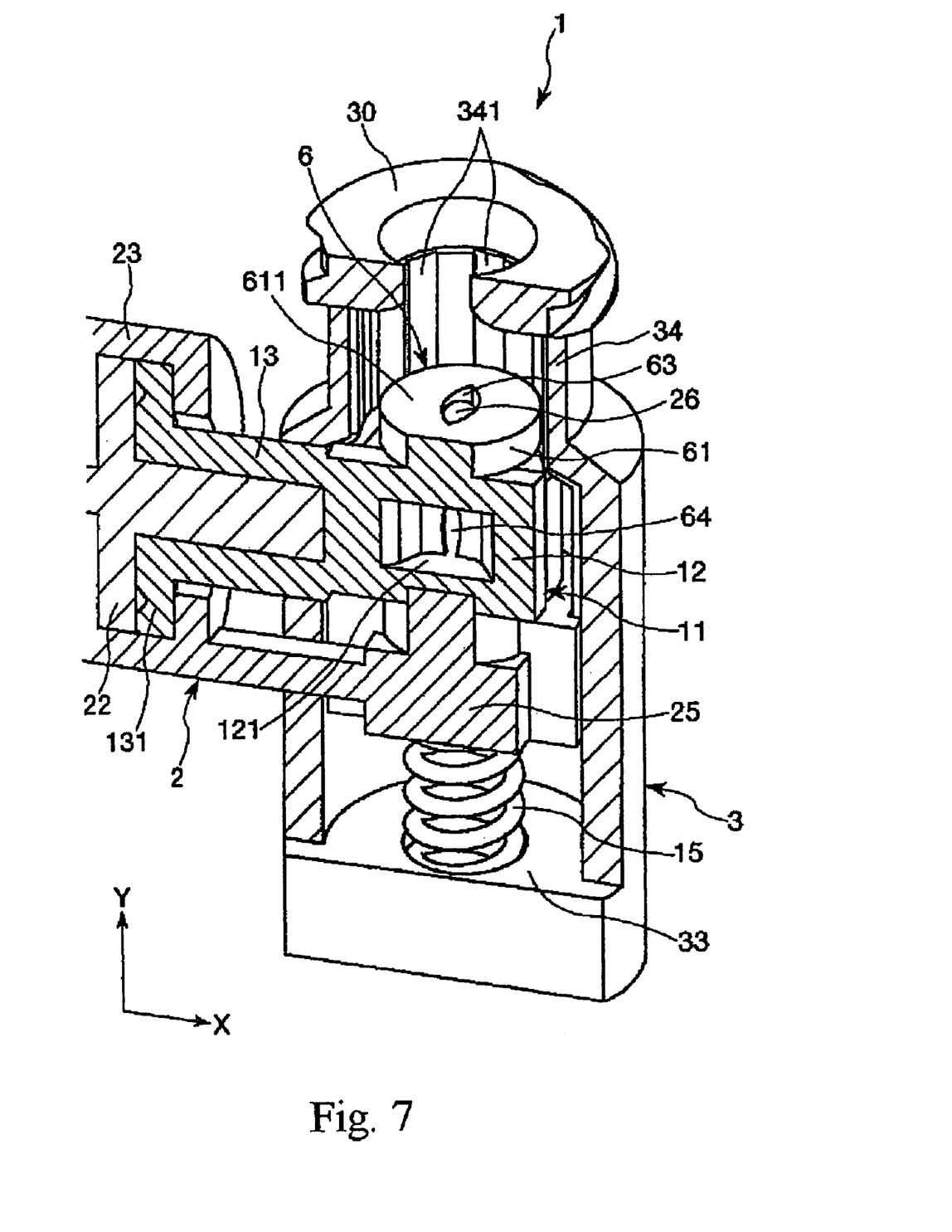
FIG. 7 is a sectional perspective view of the connector shown in FIG. 1.

As shown in FIG. 6, for connecting the male lure 100 to the first female joint port 30, the housing 3 is gripped and the tip end of the male lure 100 is inserted into the first female joint port 30. The tip end face of the male lure 100 presses the top surface 611 of the first valve body 6, compressing the helical spring 15 and moving the housing 3, the first valve body 6 (the valve assembly 11), and the support body 2 relatively in the Y-axis direction. At this time, since the first valve body 6 is slightly compressed in the Y-axis direction, the pin 26 is inserted into the top slit 63 and spreads it apart, as shown in FIG. 7. At the same time, the barrel 62 is compressed in the Y-axis direction, spreading the side slit 64, as shown in FIGS. 7 and 8. The tip end of the pin 26 is rounded to allow it to be inserted smoothly into the top slit 63.

As shown in FIG. 6, a flow passage 101 in the male lure 100 is held in fluid communication with the flow passage 51 in the male joint member 50 through the top slit 63, the side slit 64, and the liquid passage space 121.

The male lure 100 is fixed by being fitted in the inner circumferential surface of the first female joint port 30. The first female joint port 30 has an externally threaded outer circumferential surface. The male lure 100 can thus reliably be fixed by a screw lock 110 threaded over the externally threaded outer circumferential surface.

Figure 8:
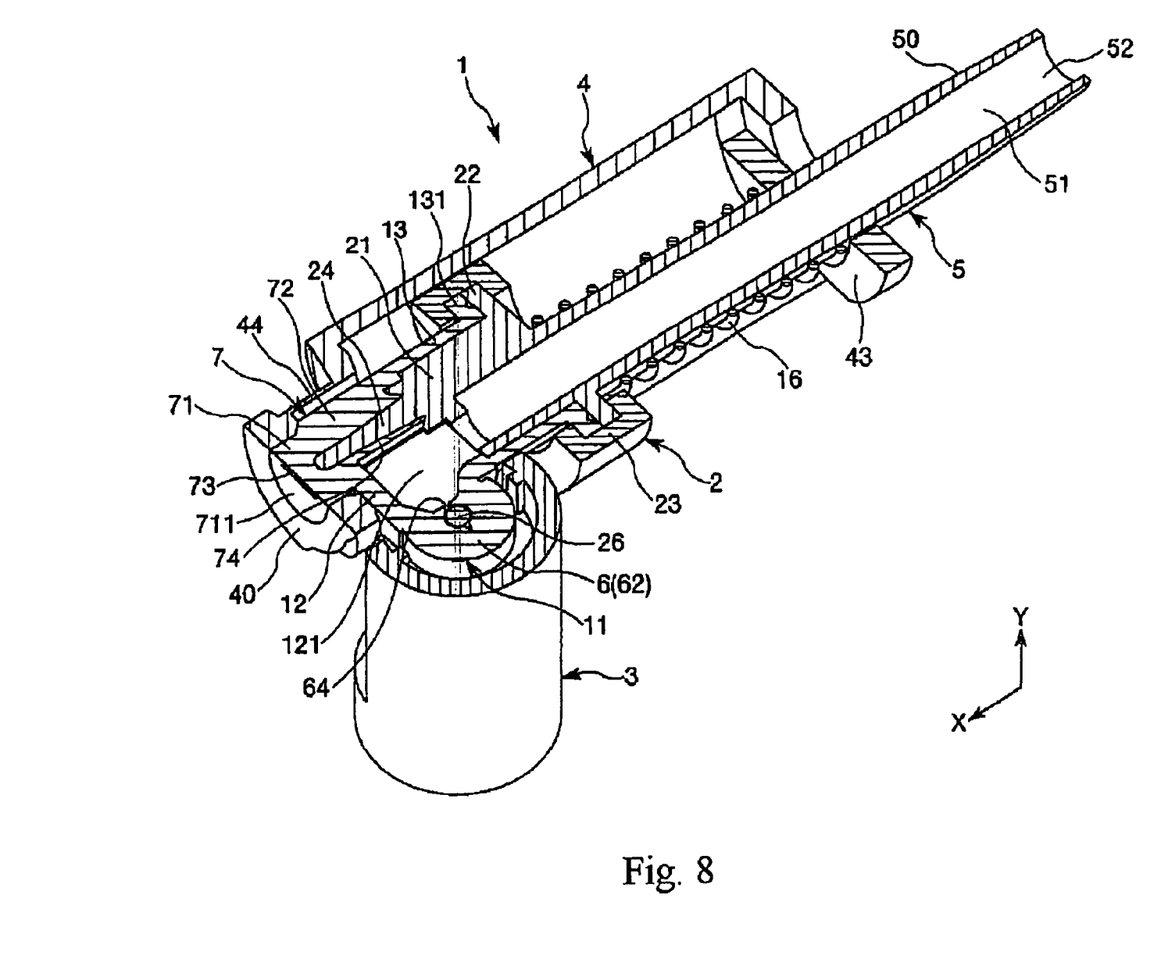
FIG. 8 is a sectional perspective view of the connector shown in FIG. 1.

In a connected state shown in FIGS. 6 through 8, when a liquid such as a medicinal solution or the like flows in from the flow passage 101 in the male lure 100, the liquid passes successively through the top slit 63, the side slit 64, the liquid passage space 121, and the flow passage 51 in the male joint member 50, and flows out of an opening 52 of the male joint member 50. At this time, as can be seen most clearly in FIG. 8, the side slit 74 facing the liquid passage space 121 is closed to prevent the liquid from flowing into the second valve body 7. Since the liquid passage space 121 is of a shape for preventing the liquid from being trapped (a shape free of bays), almost all the liquid flowing in from the flow passage 101 in the male lure 100 flows into the male joint member 50 without being trapped.

When air in the liquid passage space 121 is to replaced with a liquid such as a medicinal solution or the like, air is less likely to remain in the liquid passage space 121, and can be replaced reliably with the liquid, i.e., the connection 1 can be primed reliably.

When the male lure 100 is removed from the connected state shown in FIGS. 6 through 8, the housing 3 is restored under the restoring force of the helical spring 15 to the position where the inner circumferential surface of the first female joint port 30 tightens the top 61 of the first valve body 6. The top slit 63 and the side slit 64 are now closed, bringing the connector 1 back to the unconnected state shown in FIGS. 2 and 5.

A state of the connector 1 when the male lure 200 such as those used in a fluid infusion set is connected to the second female joint port 40 will be described below with reference to FIG. 9.

Figure 9:
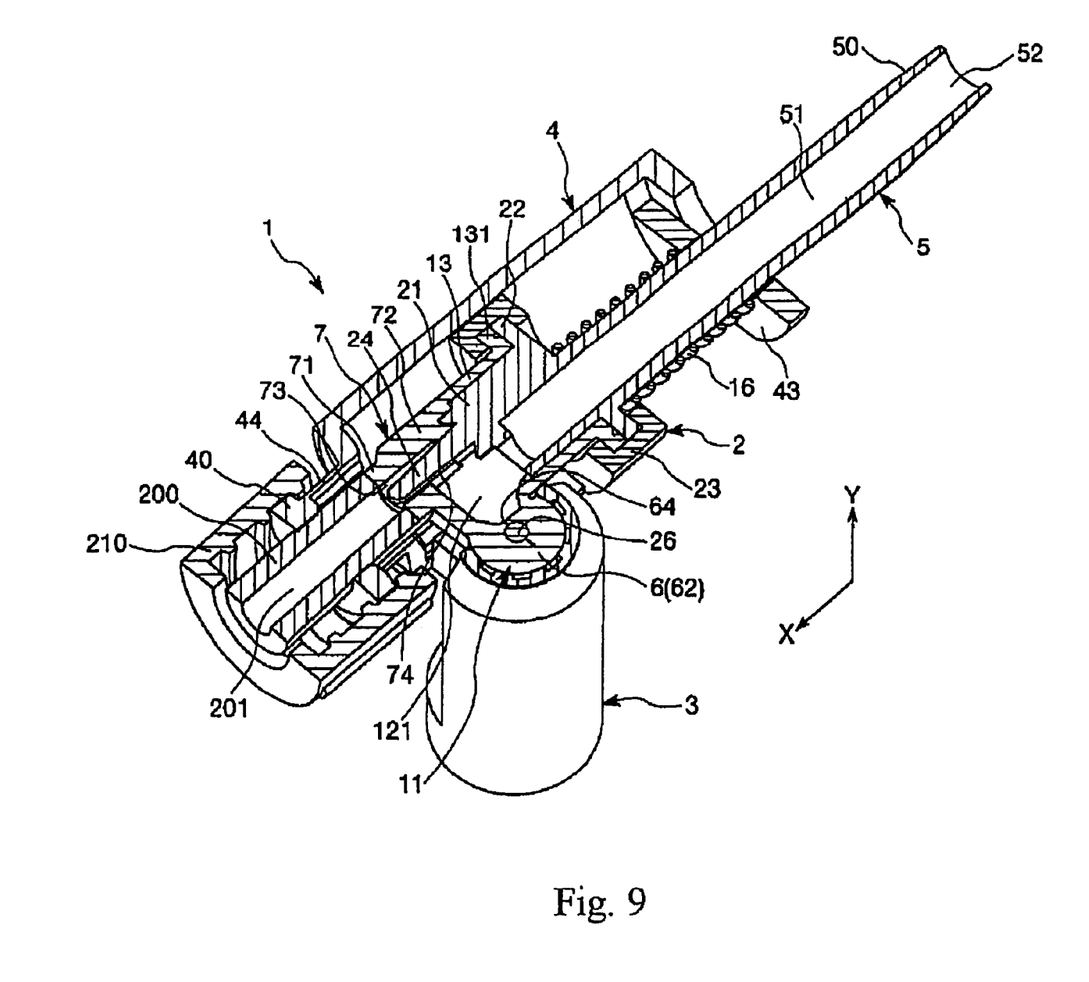
FIG. 9 is a sectional perspective view of the connector shown in FIG. 1.

As shown in FIG. 9, for connecting the male lure 200 to the second female joint port 40, the housing 4 is gripped and the tip end of the male lure 200 is inserted into the second female joint port 40. The tip end face of the male lure 200 presses the top surface 711 of the second valve body 7, compressing the helical spring 16 and moving the housing 4, the second valve body 7 (the valve assembly 11), and the support body 2 relatively in the Y-axis direction. At this time, since the second valve body 7 is slightly compressed in the X-axis direction, the pin 24 is inserted into the top slit 73 and spreads it apart. At the same time, the barrel 72 is compressed in the X-axis direction, so that the side slit 74 spreads. A flow passage 201 in the male lure 200 is held in fluid communication with the flow passage 51 in the male joint member 50 through the top slit 73, the side slit 74, and the liquid passage space 121. The tip end of the pin 24 is rounded to allow it to be inserted smoothly into the top slit 73.

The male lure 200 is fixed by being fitted in the inner circumferential surface of the second female joint port 40. The second female joint port 40 has an externally threaded outer circumferential surface. The male lure 200 can thus reliably be fixed by a screw lock 210 threaded over the externally threaded outer circumferential surface.

In such a connected state, when a liquid such as a medicinal solution or the like flows in from the flow passage 201 in the male lure 200, the liquid passes successively through the top slit 73, the side slit 74, the liquid passage space 121, and the flow passage 51 in the male joint member 50, and flows out of the opening 52 of the male joint member 50. At this time, the side slit 64 facing the liquid passage space 121 is closed to prevent the liquid from flowing into the first valve body 6. Since the liquid passage space 121 is of a shape for preventing the liquid from being trapped (a shape free of bays), almost all the liquid flowing in from the flow passage 201 in the male lure 200 flows into the male joint member 50 without being trapped.

When the male lure 200 is removed from the connected state, the housing 4 is restored under the restoring force of the helical spring 16 to the position where the inner circumferential surface of the second female joint port 40 tightens the top 71 of the second valve body 7. The top slit 73 and the side slit 74 are now closed, bringing the connector 1 back to the unconnected state shown in FIG. 2.

In the above description, the male lures 100, 200 are connected to one of the first female joint port 30 and the second female joint port 40. However, the connector 1 may be used by connecting the male lures 100, 200 simultaneously to the first female joint port 30 and the second female joint port 40.

With the connector 1 described above, inasmuch as the housings 3, 4 are movable respectively with respect to the first valve body 6 and the second valve body 7 which are fixed to the support body 2, any change caused in the volume of the liquid passage space 121 before and after the male lures 100, 200 are attached or detached is extremely small. Consequently, when the male lures 100, 200 are connected, the liquid in the flow passage 51 is prevented from being pushed out of the opening 52 (positive flow), or conversely when the male lures 100, 200 are removed, the liquid is prevented from being drawn from the opening 52 into the flow passage 51 (backward flow). Drawbacks caused by these flows are thus prevented.

According to the present invention, the liquid passage portion 12, the first valve body 6, and the second valve body 7 should preferably be integrally formed as with the embodiment, though they may be separate members. The integral structure makes it possible to provide the liquid passage space 121 with a smooth inner wall for more reliably preventing the liquid from being trapped therein.

The urging means for urging the first valve body 6 and the second valve body 7 are not limited to the helical springs 15, 16, but may be other springs. The material of the urging means is not limited to a metal material such as stainless steel or the like, but may be a rubber material such as silicone rubber or the like. If the urging means are made of a rubber material, then they may be integrally formed with the first valve body 6 and the second valve body 7.

The material of the support body 2, the housings 3, 4, and the tubular member 5 (the male joint member 50) is not limited to any particular materials, but should preferably be a material having suitable hardness, e.g., any of various polymer materials such as polyethylene, polypropylene, polycarbonate, or the like.

In the present embodiment, the connector has two female joint ports. However, the connector according to the present invention may have one female joint port or three or more female joint ports.

Although the connector according to the present invention has been described above with respect to the illustrated embodiment, the connector is not limited to the illustrated embodiment, but the various parts of the connector may be replaced with parts of any desired structures which are capable of performing the same functions. Furthermore, any desired structures may be added to the connector.

INDUSTRIAL APPLICABILITY

With the connector according to the present invention, as the flow passage is reliably opened and closed when the tube is connected and disconnected, the flow passage is prevented from being contaminated. The liquid is prevented from being trapped in the connector. Therefore, the connector according to the present invention has industrial applicability.

The invention claimed is:

1. A connector comprising:
    a tubular male joint member;
    a liquid passage portion having a liquid passage space defined therein in fluid communication with an interior of said male joint member;
    a first female joint port and a second female joint port each of which is capable of receiving a tube;
    a first valve body made of an elastic material, said first valve body comprising a top, a bottom, and a side wall extending between the top and bottom, having a top slit defined in the top thereof and a side slit defined in the side wall thereof, said first valve body being deformable to open said top slit and said side slit when the tube is connected to said first female joint port; and
    a second valve body made of an elastic material and having a top slit defined in a top thereof and a side slit defined in a side thereof, said second valve body being deformable to open said top slit and said side slit when the tube is connected to said second female joint port;
    wherein said side slit of said first valve body and said side slit of said second valve body face said liquid passage space;
    when the tube is connected to said first female joint port, an interior of the tube and the interior of said male joint member communicate with each other through said top slit and said side slit of said first valve body and said liquid passage space; and
    when the tube is connected to said second female joint port, an interior of the tube and the interior of said male joint member communicate with each other through said top slit and said side slit of said second valve body and said liquid passage space.

2. A connector according to claim 1, wherein said first female joint port or said second female joint port and said male joint member have respective central lines extending substantially parallel to each other.

3. A connector according to claim 1, wherein said liquid passage portion, said first valve body, and said second valve body are integrally formed with each other.

4. A connector according to claim 1, wherein at least one of said first female joint port and said second female joint port is axially movable relatively to the corresponding valve body.

5. A connector according to claim 1, wherein said first valve body and said second valve body have respective central lines, which are skew lines.

6. A connector according to claim 5, wherein said first female joint port is axially movable relatively to said first valve body, and said second female joint port is axially movable relatively to said second valve body.

7. A connector comprising:
    a tubular male joint member;
    a liquid passage portion having a liquid passage space defined therein in fluid communication with an interior of said male joint member;
    a housing having a female joint port which is capable of receiving a tube; and
    a valve body made of an elastic material and housed in said housing, said valve body being fixedly disposed with respect to said male joint member, said valve body comprising a top, a bottom, and a side wall extending between the top and bottom, having a top slit defined in the top thereof and a side slit defined in the side wall thereof, said valve body, said valve body being deformable to open said top slit and said side slit when the tube is connected to said female joint port;

wherein said side slit of said valve body faces said liquid passage space;

said housing is axially movable relatively to said valve body;

when the tube is to be connected to said female joint port, said housing is moved with respect to said valve body to insert the tube into said female joint port; and when the tube is connected to said female joint port, an interior of the tube and the interior of said male joint member communicate with each other through said top slit and said side slit of said valve body and said liquid passage space.

8. A connector according to claim 1, further comprising a solid pin for being inserted into said top slit to spread said top slit when the tube is connected.

9. A connector comprising:

a tubular male joint member;

a liquid passage portion having a liquid passage space defined therein in fluid communication with an interior of said male joint member;

a female joint port which is capable of receiving a tube;

a valve body made of an elastic material, said valve body comprising a top, a bottom, and a side wall extending between the top and bottom, having a top slit defined in the top thereof and a side slit defined in the side wall thereof, and a hollow space, said valve body being deformable to open said top slit and said side slit when the tube is connected to said female joint port; and a solid pin positioned in the hollow space of said valve body;

wherein said side slit of said valve body faces said liquid passage space;

when the tube is connected to said female joint port, the tube presses a top surface of said valve body to compress said valve body axially, thereby opening said side slit and inserting said pin into said top slit to spread said top slit, so that an interior of the tube and the interior of said male joint member communicate with each other through said top slit and said side slit of said valve body and said liquid passage space.

10. A connector according to claim 1, wherein said liquid passage space is of a shape for preventing a liquid from being trapped therein when the liquid flows in said liquid passage space.

11. A connector according to claim 2, wherein said liquid passage portion, said first valve body, and said second valve body are integrally formed with each other.

12. A connector according to claim 2, wherein at least one of said first female joint port and said second female joint port is axially movable relatively to the corresponding valve body.

13. A connector according to claim 2, wherein said first valve body and said second valve body have respective central lines, which are skew lines.

14. A connector according to claim 2, further comprising a solid pin for being inserted into said top slit to spread said top slit when the tube is connected.

15. A connector according to claim 7, further comprising a solid pin for being inserted into said top slit to spread said top slit when the tube is connected.

16. A connector according to claim 2, wherein said liquid passage space is of a shape for preventing a liquid from being trapped therein when the liquid flows in said liquid passage space.

17. A connector according to claim 7, wherein said liquid passage space is of a shape for preventing a liquid from being trapped therein when the liquid flows in said liquid passage space.

18. A connector according to claim 9, wherein said liquid passage space is of a shape for preventing a liquid from being trapped therein when the liquid flows in said liquid passage space.

* * * * *

UNITED STATES PATENT AND TRADEMARK OFFICE
CERTIFICATE OF CORRECTION

PATENT NO. : 7,484,529 B2
APPLICATION NO. : 10/577832
DATED : February 3, 2009
INVENTOR(S) : Takayuki Yokota et al.

It is certified that error appears in the above-identified patent and that said Letters Patent is hereby corrected as shown below:

Claim 7, Column 10, Line 67: Same phrase printed twice: remove "said valve body". (Should read: thereof, said valve body being . . .)

Signed and Sealed this

Twenty-fifth Day of August, 2009

David J. Kappos
*Director of the United States Patent and Trademark Office*